(12) United States Patent
Bach et al.

(10) Patent No.: US 7,419,947 B2
(45) Date of Patent: Sep. 2, 2008

(54) PROCESS FOR PREPARING GRANULES WITH FILAMENTOUS COATINGS

(75) Inventors: Poul Bach, Birkerod (DK); Ole Simonsen, Soborg (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 10/397,986

(22) Filed: Mar. 26, 2003

(65) Prior Publication Data

US 2003/0220220 A1   Nov. 27, 2003

Related U.S. Application Data

(60) Provisional application No. 60/391,839, filed on Jun. 27, 2002.

(30) Foreign Application Priority Data

Mar. 27, 2002   (DK)   ............... 2002 00473

(51) Int. Cl.
*C11D 11/00* (2006.01)
*C11D 7/42* (2006.01)
*C12N 9/98* (2006.01)

(52) U.S. Cl. .............. 510/441; 510/442; 510/392; 510/475; 435/184; 435/187

(58) Field of Classification Search ........... 510/441, 510/442, 392, 475; 435/184, 187
See application file for complete search history.

(56) References Cited

U.S. PATENT DOCUMENTS

| | | | | |
|---|---|---|---|---|
| 3,773,674 A | * | 11/1973 | Adam et al. ............... | 510/374 |
| 4,973,422 A | * | 11/1990 | Schmidt .................... | 510/337 |
| 5,093,021 A | * | 3/1992 | Coyne et al. ............... | 510/530 |
| 5,209,863 A | * | 5/1993 | Dixit et al. ................ | 510/223 |
| 5,258,132 A | * | 11/1993 | Kamel et al. .............. | 510/370 |
| 5,324,649 A | * | 6/1994 | Arnold et al. ............. | 435/187 |
| 5,733,763 A | * | 3/1998 | Markussen et al. ........ | 435/175 |
| 5,801,033 A | * | 9/1998 | Hubbell et al. ............ | 435/182 |
| 5,814,501 A | * | 9/1998 | Becker et al. ............. | 435/174 |
| 6,268,329 B1 | * | 7/2001 | Markussen ................. | 510/392 |
| 6,310,027 B1 | * | 10/2001 | Dale .......................... | 510/392 |
| 6,528,470 B1 | * | 3/2003 | Ha et al. .................... | 510/311 |
| 6,534,466 B2 | * | 3/2003 | Christensen, Jr. .......... | 510/392 |
| 6,602,843 B2 | * | 8/2003 | Markussen ................. | 510/392 |
| 7,070,820 B2 | * | 7/2006 | Simonsen et al. .......... | 426/96 |

FOREIGN PATENT DOCUMENTS

| | | |
|---|---|---|
| EP | 0 304 332 | 2/1989 |
| JP | 62269686 A * | 11/1987 |
| WO | WO 97 23606 | 7/1997 |
| WO | WO 00 40689 | 7/2000 |
| WO | WO 01 25323 | 4/2001 |

* cited by examiner

*Primary Examiner*—Lorna M Douyon
(74) *Attorney, Agent, or Firm*—Michael W. Krenicky

(57) ABSTRACT

The present invention relates to a granule comprising a core and a coating, wherein the core comprises an active compound, and the coating comprises filaments prepared from atomizing a liquid coating composition having the property that liquid coating composition forms filaments upon atomization.

30 Claims, No Drawings

US 7,419,947 B2

PROCESS FOR PREPARING GRANULES WITH FILAMENTOUS COATINGS

CROSS-REFERENCE TO RELATED APPLICATIONS

This application claims priority under 35 U.S.C. 119 of Danish application PA 2002 00473 filed Mar. 27, 2002 and U.S. Provisional application No. 60/391,839 filed Jun. 27, 2002, the contents of which are fully incorporated herein by reference.

FIELD OF THE INVENTION

The present invention relates to particles comprising a core and a coating, wherein said core comprises an active compound and said coating comprises filamentous substance. The coating of the present invention serves both the purpose of regulating density of the particles and protecting the particle from damage by being able of absorbing impacts on the particle. The invention further relates to a process for the manufacture of such coated particles and to a process for the manufacture of said filamentous substance.

BACKGROUND OF THE INVENTION

It is known to the art to incorporate active compounds such as enzymes into dry solid particles or granules and thereby protect the active compound from inactivation and/or protect the environment from the active compound. Such particles or granules have usually been applied to other dry products such as dry granular detergent compositions to improve their performance. Enzymes are an example of an active compound, which may be incorporated in dry solid particles or granules.

Known enzyme granule formulation technologies include:

a) Spray dried products, wherein a liquid enzyme-containing solution is atomized in a spray drying tower to form small droplets which during their way down the drying tower dry to form a continuous film layer which encapsulate the enzyme-containing particles. Very small particles can be produced this way (Michael S. Showell (editor); *Powdered detergents*; Surfactant Science Series; 1998; vol. 71; page 140-142; Marcel Dekker).

b) Layered products, wherein the enzyme is coated as a layer around a pre-formed inert core particle, wherein an enzyme-containing solution is atomized, typically in a fluid bed apparatus wherein the pre-formed core particles are fluidised, and the enzyme-containing solution adheres to the core particles and dries up to leave a layer of dry enzyme on the surface of the core particle. Particles of a desired size can be obtained this way if a useful core particle of the desired size can be found. This type of product is described in e.g. WO 97/23606 c) Absorbed core particles, wherein rather than coating the enzyme as a layer around the core, the enzyme is absorbed onto and/or into the surface of the core. Such a process is described in WO 97/39116.

d) Extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme. (Michael S. Showell (editor); *Powdered detergents*; Surfactant Science Series; 1998; vol. 71; page 140-142; Marcel Dekker)

e) Prilled products, wherein an enzyme powder is suspended in molten wax and the suspension is sprayed, e.g. through a rotating disk atomizer, into a cooling chamber where the droplets quickly solidify (Michael S. Showell (editor); *Powdered detergents*; Surfactant Science Series; 1998; vol. 71; page 140-142; Marcel Dekker). The product obtained is one wherein the enzyme is uniformly distributed throughout an inert material instead of being concentrated on its surface. Also U.S. Pat. No. 4,016,040 and U.S. Pat. No. 4,713,245 are documents relating to this technique f) Mixer granulation products, wherein an enzyme-containing liquid is added to a dry powder composition of conventional granulating components. The liquid and the powder in a suitable proportion are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 (NOVO NORDISK) and related documents EP 170360 B1 (NOVO NORDISK), EP 304332 B1 (NOVO NORDISK), EP 304331 (NOVO NORDISK), WO 90/09440 (NOVO NORDISK) and WO 90/09428 (NOVO NORDISK). In a particular product of this process wherein various high-shear mixers can be used as granulators, granulates consisting of the enzyme, fillers and binders etc. are mixed with cellulose fibers to reinforce the particles to give the so-called T-granulate. Reinforced particles, being more robust, release less enzymatic dust (vide infra).

Known enzyme formulations are to day either "dry formulations", i.e. consisting of agglomerates of solid particles, or "liquid formulations", i.e. liquids containing solutions or suspensions of enzymes/enzyme particles.

WO 01/25322 discloses a foam component, which comprises a mixture of a polymeric material, a dissolution aid and an active ingredient.

WO 01/24990 discloses a process for preparing a foam component, said process comprises the steps of extruding a viscous mixture from a rotating extrusion plate onto a receiving surface.

WO 01/25323 discloses elastic articles comprising a polymeric material and an active ingredient.

SUMMARY OF THE INVENTION

Reasons for formulating active compounds into particles, such as preparing enzyme granules include (1) protection of the active compound by separating it from the surrounding potentially hostile environment until the moment when the active compound is to be used in an application and (2) reduction of potentially harmful dust which may be generated from the active compound. Said protection of the active compound and reduction of dust formation may, in accordance with prior art be aided or improved by coating particles.

Particles such as enzyme granules are typically valued and traded on the market according to weight or activity of the active compound per weight of preparation therefore it is desirable to employ lightweight coating materials. However, the coating material must also provide the aforesaid necessary properties and functionalities to the particle or granule on which it is coated or preferably improve such properties and functionalities.

Hence one object of the present invention is to provide coated particles comprising an active compound, wherein the coating is lightweight, but in addition also provide both adequate protection of the active compound in the particles and an acceptable low release of active dust from the particles upon handling.

We have found that coating materials comprising substances on a filamentous form may act as good coating materials, because they are potentially of light weight due to the possible porous filamentous network structure providing lots of gas pockets. Furthermore we have found that substances on a filamentous form may provide elasticity to the coating, thereby making the coated particle resistant to physical strain imposed on the particles, e.g. during manufacture, packaging and transportation, where particles are often exposed to rough handling. Hence coatings comprising a substance on a filamentous form, due to its potential elasticity and its potential ability to absorb physical strain and/or impacts may prevent and/or reduce breakage of the particles and thus both protect the active compound and prevent and/or reduce dust formation.

We have further found that at certain conditions it is possible to bring substances on a filamentous form by atomizing a liquid coating composition comprising the substance and said filamentous substances prepared in this manner result in excellent coating materials which in fact possesses the above mentioned desired potential properties of being both lightweight and elastic.

Hence, the present invention provides granules comprising a core and a coating, wherein the core comprises an active compound and the coating comprises filaments prepared from atomizing a liquid coating composition having the property that said liquid coating composition forms filaments upon atomization.

The invention further provides a process for preparing coated granules of the invention comprising contacting a granule comprising an active compound with a coating, wherein the coating comprises filaments prepared from atomizing a liquid coating composition having the property that said liquid coating composition form filaments upon atomization.

The invention also provides coated granules, wherein the coating comprises at least 40% w/w of a substance on filamentous form.

The invention further provides a process for preparing coated granules comprising contacting, in a mixer apparatus or a roller device or by means of a spraying device, a particle comprising an active compound with a coating material comprising at least 40% w/w of filaments.

The invention further provides compositions comprising the granules of the invention and uses of said granules.

DETAILED DESCRIPTION OF THE INVENTION

When handling solid particles comprising an active compound, one of the major problems is the formation of dust from the active compound, which may be harmful to persons handling the dry solid composition.

Although the active compound may be incorporated in dry solid particles as known to the art, which may inhibit the formation of active dust it is a fact that conventional particles are usually solid and brittle which makes them susceptible to damage when a strain is applied to them, which might happen during handling such as manufacture, packaging and transportation.

It is presently contemplated that active dust is released when the integrity of such solid particles is damaged, e.g. when a solid particle breaks or cracks. This may happen when the solid particle is subjected to strain such as impact e.g. during handling. The strain/impact will cause a corresponding stress building up in the solid particle to counter act the strain/impact. Upon increasing the strain the build up of stress in the particle to counteract the strain may continue to a certain point (the yield point) depending on the particle material. However, if the strain is greater than the forces upholding the integrity of the solid particle (the yield point) the solid particle is no longer able of counter acting the strain and the strain will cause damage to the physical integrity of the solid particle, which may release active compounds from the solid particle as dust.

Definitions

The terms "particles" and "granules" are to be understood as a predominantly spherical or near spherical structure of a macromolecular size and coated particles are in the following referred to as granules.

The term "filament" is to be understood as a macromolecular object with a length to diameter ratio of at least 2, particularly with a length to diameter ratio of at least 50, more particularly with a length to diameter ratio of at least 100.

The term "liquid coating composition" is to be understood as the coating feed to be used in the production of filaments. The liquid coating composition comprises a solvent, particularly water, and coating materials e.g. a polymer.

The term "true density" of a compound as used herein, is to be construed as the density in weight per volume of said compound, determined by immersing a weighed amount of the compound in a liquid in which the compound is insoluble and measuring the volume increase of liquid dispersion (i.e. the volume of liquid which is displaced by the compound). As an example, if 1 gram of a compound is added to a volume of 10 $cm^3$ of a liquid in which the compound is insoluble and by said addition the volume of the liquid-compound mixture increases to 11 $cm^3$, the compound thereby displacing 1 $cm^3$ of liquid, the true density of the compound is 1 gram per $cm^3$. The true density of a liquid may be measured as the weight of a measured volume of the liquid.

Introduction

Some conventional methods of coating of particles employ atomizing a liquid solution of coating material to very small single droplets, which dries on the particle to form a coherent continuous film coating layer. When coating particles according to these conventional methods it has been desired to avoid processing conditions, which could interfere with the formation of single droplets upon atomization and thereby interfere with the formation of a continuous film.

However, according to the present invention in stead of forming single droplets in atomizing a liquid coating composition, we have found that a liquid coating composition may form filaments upon atomization during coating of the cores e.g. by adjusting the molecular weight of the polymer in the liquid coating composition and/or the solid content of the liquid coating composition.

We have surprisingly found that said filaments can build up an excellent coating layer around particles which gets a "ball of yarn" like appearance. Furthermore we have found that the coating layer is constructed as a porous network and due to the construction of said coating layer it contains a significant amount of gas pockets hence it is very light and has increased elasticity and thereby exhibit improved impact resistance. Due to the light weight of the produced coating it is possible to increase the particle size with only limited increase in weight. The increased elasticity and accordingly improved impact resistance is resulting in a decrease in dust release owing to the decrease in damage of the active containing particles.

The Granule

The Core Particle

The core particle contains the active compound. Besides of the active compound the core particle may be constructed in any way or of any material, which provides the desired functional properties of the core material, e.g. the core may consist of materials, which allows readily release of the active compound upon introduction to an aqueous medium. In one embodiment the core particle is constructed of a particulate carrier (I) with the active compound absorbed and/or an enzyme containing layer (II) applied on the carrier surface, optionally comprising a protecting reducing agent. There may even be additional coating within the core material providing desired functional properties of the core material. Another core particle may be the so called T-granulate wherein the active compound and granulation material is mixed to form granules incorporating the enzyme distributed throughout the core such as described in U.S. Pat. No. 4,106,991 e.g. Example 1. Any conventional methods and non-active materials may be used to prepare the core particle. Examples of known conventional cores particles and materials is, inter alia, described in, U.S. Pat. No. 4,106,991 (in particular), EP 170360, EP 304332, EP 304331, EP 458849, EP 458845, WO 97/39116, WO 92/12645, WO 89/08695, WO 89/08694, WO 87/07292, WO 91/06638, WO 92/13030, WO 93/07260, WO 93/07263, WO 96/38527, WO 96/16151, WO 97/23606, U.S. Pat. No. 5,324,649, U.S. Pat. No. 4,689,297, EP 206417, EP 193829, DE 4344215, DE 4322229 A, DD 263790, JP 61162185 A, JP 58179492.

As a particular embodiment of the present invention the core particle may be prepared by applying a layer of active compound onto a "placebo" carrier (active-free carrier) according to the methodology described in U.S. Pat. No. 4,689,297 and U.S. Pat. No. 5,324,649. Optionally additional active compound may be absorbed into the surface of the carrier.

In a particular embodiment of the invention the core particle may also comprise a protective agent as described for the coating, vide infra, particularly mixed with the active in suitable amounts such as 0.1-1% w/w of the coated particle, particularly 0.1-0.5% w/w, e.g. 0.33% w/w. The protective agent may be an antioxidant, a reducing agent or a mixture.

In one embodiment the core particle comprises an active compound dispersed in a visco-elastic liquid matrix having a $\eta'$ and a $\eta''$ both between $10^3$ to $10^{14}$ Pa measured in a cone-and-plate rheometer at 25° C. and a sinusoidal frequencies $\omega$ of 1 Hz. The visco-elastic liquid making up the matrix wherein the active and optionally other useful components may in principle be any material or mixtures of materials which meets the requirements for viscosity and elasticity set for the visco-elastic core particles, as described in WO 02/28991.

In particular materials may be organic visco-elastic materials such as liquid materials comprising, consisting of or containing organic polymers and/or monomers. Materials such as carbohydrate polymers (e.g. pectins), proteins (e.g.) gelatin, sugars, glucose syrups, modified vegetable oils or mixtures thereof can be brought or formulated into a liquid state having visco-elastic properties as described above.

Particularly a majority of the components constituting the visco-elastic liquid matrix are water soluble.

The core particle should in particular be less than 700 µm or 800 µm, particularly between 50 and 500 µm, such as between 100 and 400 µm, most particularly between 200 and 300 µm.

In general the core particles may have a true density below 3 g/cm$^3$, preferably below 2 g/cm$^3$, more particularly below 1.5 g/cm$^3$.

Active Compound

The active compound of the invention may be any active component or mixture of active components, which benefits from being separated from the environment surrounding the particle. The term "active compound" is meant to encompass all components, which upon release from the particle upon applying the particle of the invention in a process serve a purpose of improving the process. Suitable active compounds are those, which are either subject of deactivation and/or causing deactivation to other components in the compositions of the invention. As said the active compound may be present dispersed as discrete solid particles in the core particle.

The active compound may be inorganic of nature such as bleach components as mentioned or organic. Particular active compounds are active biological compounds which are usually very sensitive to the surrounding environment such as compounds obtainable from microorganisms. More particular active compounds are peptides or polypeptides or proteins. Most particular are proteins such as enzymes.

The enzyme in the context of the present invention may be any enzyme or combination of different enzymes. Accordingly, when reference is made to "an enzyme" this will in general be understood to include combinations of one or more enzymes.

It is to be understood that enzyme variants (produced, for example, by recombinant techniques) are included within the meaning of the term "enzyme". Examples of such enzyme variants are disclosed, e.g., in EP 251,446 (Genencor), WO 91/00345 (Novo Nordisk), EP 525,610 (Solvay) and WO 94/02618 (Gist-Brocades NV).

The enzyme classification employed in the present specification with claims is in accordance with *Recommendations (1992) of the Nomenclature Committee of the International Union of Biochemistry and Molecular Biology*, Academic Press, Inc., 1992.

Accordingly the types of enzymes which may appropriately be incorporated in granules of the invention include oxidoreductases (EC 1.-.-.-), transferases (EC 2.-.-.-), hydrolases (EC 3.-.-.-), lyases (EC 4.-.-.-), isomerases (EC 5.-.-.-) and ligases (EC 6.-.-.-).

Preferred oxidoreductases in the context of the invention are peroxidases (EC 1.11.1), laccases (EC 1.102.2) and glucose oxidases (EC 1.1.3.4)]. An Example of a commercially available oxidoreductase (EC 1.-.-.-) is GLUZYME® (enzyme available from Novozymes A/S). Further oxidoreductases are available from other suppliers. Preferred transferases are transferases in any of the following sub-classes:

a) Transferases transferring one-carbon groups (EC 2.1);
b) transferases transferring aldehyde or ketone residues (EC 2.2); acyltransferases (EC 2.3);
c) glycosyltransferases (EC 2.4);
d) transferases transferring alkyl or aryl groups, other that methyl groups (EC 2.5); and
e) transferases transferring nitrogeneous groups (EC 2.6).

A most preferred type of transferase in the context of the invention is a transglutaminase (protein-glutamine gamma-glutamyltransferase; EC 2.3.2.13).

Further examples of suitable transglutaminases are described in WO 96/06931 (Novo Nordisk A/S).

Preferred hydrolases in the context of the invention are: Carboxylic ester hydrolases (EC 3.1.1.-) such as lipases (EC 3.1.1.3); phytases (EC 3.1.3.-), e.g. 3-phytases (EC 3.1.3.8) and 6-phytases (EC 3.1.3.26); glycosiciases (EC 3.2, which fall within a group denoted herein as "carbohydrases", such as alpha-amylases (EC 3.2.1.1); peptides (EC 3.4, also known as proteases); and other carbonyl hydrolases].

In the present context, the term "carbohydrase" is used to denote not only enzymes capable of breaking down carbohydrate chains (e.g. starches or cellulose) of especially five- and six-membered ring structures (i.e. Glycosiciases, EC 3.2), but also enzymes capable of isomerizing carbohydrates, e.g. six-membered ring structures such as D-glucose to five-membered ring structures such as D-fructose.

Carbohydrases of relevance include the following (EC numbers in parentheses): alpha-amylases (EC 3.2.1.1), -beta-amylases (EC 3.2.1.2), glucan 1,4alpha-glucosidases (EC 3.2.1.3), endo-1,4-beta-glucanase (cellulases, EC 3.2.1.4), endo-1,3(4) -beta-glucanases (EC 3.2.1.6), endo-1,4-beta-xylanases (EC 3.2.1.8), dextrariases (EC 3.2.1.11), chitinases (EC 3.2.1.14), polygalacturonases (EC 3.2.1.15), lysozymes (EC 3.2.1.17), -beta-glucosidases (EC 3.2.1.21), alpha-galactosidases (EC 3.2.1.22), -beta-galactosidases (EC 3.2.1.23), amylo-1,6-glucosidases (EC 3.2.1.33), xylan 1,4-beta-xylosidases (EC 3.2.1.37), glucan endo-1,3-beta -D-glucosidases (EC 3.2.1.39), alpha-dextrin endo-1,6alpha-glucosidases (EC3.2.1.41), sucrose alpha-glucosidases (EC 3.2.1.48), glucan endo-1,3alpha-glucosidases (EC 3.2.1.59), glucan 1,4-beta-glucosidases (EC 3.2.1.74), glucan endo-1, 6-beta-glucosidases (EC 3.2.1.75), arabinan endo-1,5-alpha-L-arabinosidases (EC 3.2.1.99), lactases (EC 3.2.1.108), chitosanases (EC 3.2.1.132) and xylose isomerases (EC 5.3.1.5).

Examples of commercially available proteases (peptidases) include KANNASE™, EVERLASE™, ESPERASE™, ALCALAS™, NEUTRASE™, DURAZYM™, SAVINASE™, PYRASE™, Pancreatic Trypsin NOVO (PTN), BIO-FEED☐ PRO and CLEAR -LENS™ PRO (all available from Novozymes A/S).

Other commercially available proteases include MAX-ATASE™, MAXACAL™, MAXAPEM™, OPTICLEAN™ and PURAFECT™ (available from Genencor International Inc. or DSM).

Examples of commercially available lipases include LIPOPRIME™μLIPOLASE™, LIPOLASE™ ULTRA, LIPOZYME™, PALATASE™, NOVOZYM™ 435 and LECITASE™ (all available from Novoxyrnes A/S)

Other commercially available lipases include LUMAFASt™ (Pseudon,anas mendocina lipase from Genencor International Inc.); LIPOMAX™ (Ps. pseudoaloallgenes lipase from DSM/Genencor Int Inc.; and Bacillus ap. lipase from Genencor). Further lipases are available from other suppliers.

Examples of commercially available carbohydrases include ALPHA-GAL™, BIO -FEED™ ALPHA, BIO-FEED™ BETA, BIO-FEED™ PLUS, BIO-FEED™ PLUS, NOVOZYME™ 188, CELLUCLAST™, CELLUSOF™, CEREMYL™, CITROZYM™, DENIMAX™, DEZYME™, DEXTROZYME™, FINIZYM™, FUNGAMYL™, GAMANASE™, GLUCANEX™, LACTOZYM™, MALTOGENASE™, PENTOPAN™, PECTINEX™, PROMOZYME™, PULPZYME™, NOVAMYL™, TERMAMYL™, AMG™ (Amyloglucosidase Novo), MALTOGENASE™SWEETZYME™ and AQUAZYM™ (all available from Novazymes A/S. Further carbohydrases are available from other suppliers.

The Coating

Filaments

The filaments of the present invention are prepared from a liquid coating composition. Said liquid coating composition comprises one or more coating substances, preferably dissolved in the liquid coating composition. In a particular embodiment of the present invention the liquid coating composition comprises a dissolved polymer in an aqueous solution. The liquid coating composition may further comprise auxiliary coating materials.

Coating Substances

The coating substances suitable for this invention are dissolved polymers in solutions which are able to form filaments when atomized. Said polymers are selected from but are not limited to the group consisting of waxes, polypeptides, carbohydrate polymers and synthetic polymers. In a particular embodiment of the present invention the liquid coating composition comprises between 1 to 95 wt % of polymer, in a more particular embodiment of the present invention the liquid coating composition comprises between 25 to 75 wt % of polymer.

In a particular embodiment of the present invention the polymer has a molecular weight above 1,000. In a more particular embodiment of the present invention the polymer has a molecular weight above 10,000. In a more particular embodiment the polymer has a molecular weight above 100,000.

In a particular embodiment the liquid is water. In another particular embodiment the polymer is soluble in water.

Waxes:

The term wax as used herein is to be understood as a compound having a melting point between 20-150° C. Preferred waxes are organic compounds or salts of organic compounds having a melting point in the said range. In the context of the invention the term wax as used herein also encompasses mixtures of two or more different waxes. Also, an important feature of the wax or mixture of waxes is that the wax should be water soluble or water dispersible, particularly in neutral and alkaline solution, so that when the coated particles of the invention is introduced into an aqueous solution, i.e. by diluting it with water, the wax should disintegrate and/or dissolve providing a quick release and dissolution of the active compound incorporated in the particles to the aqueous solution. Examples of water soluble waxes are poly ethylene glycols (PEG's). Accordingly amongst water soluble waxes the solubility of wax in water should in particular be up to 75 parts wax to 25 parts water.

The wax of the invention may be any wax, which is chemically synthesized. It may also equally well be a wax isolated from a natural source or a derivative thereof. Accordingly, the wax of the invention may be selected from the following non limiting list of waxes:

Poly ethylene glycols, abbreviated PEG, type of wax. Different PEG waxes are commercially available having different molecular sizes.

polypropylens or polyethylens or mixtures thereof.

Nonionic tensides which are solid at room temperature such as ethoxylated fatty alcohols having a high level of ethoxy groups such as Lutensol AT80 from BASF having 80 units of ehtyleneoxide per molecule. Alternatively polymers of ethyleneoxide, propyleneoxide or copolymers thereof are useful, such as in block polymers, e.g. Pluronic PE 6800 from BASF Germany.

Waxes isolated from a natural source, such as Carnauba wax, Candelilla wax and bees wax. Other natural waxes or derivatives thereof are waxes derived from animals or plants, e.g. of marine origin.

Fatty acid alcohols, such as the linear long chain fatty acid alcohol NAFOL 1822 ($C_{18, 20, 22}$) from Condea Chemie GMBH Germany, having a true density of about 0.96 g/cm$^3$.

Mono-glycerides and/or di-glycerides, such as glyceryl stearate, wherein stearate is a mixture of stearic and palmitic acid, are useful waxes. An example of this is Dimodan PM—from Danisco Ingredients, Denmark—having a true density of about 1 g/cm$^3$ Fatty acids, such as hydrogenated linear long chained fatty acids.

Paraffines, i.e. solid hydrocarbons.

Micro-crystalline wax.

In further embodiments waxes which are useful in the invention can be found in C. M. McTaggart et. al., Int. J. Pharm. 19, 139 (1984) or Flanders et.al., Drug Dev. Ind. Pharm. 13, 1001 (1987) both incorporated herein by reference.

Polypeptide:

The poylpeptide may be selected from gelatin, collagen, casein, chitosan poly aspartic acid and poly glutamic acid.

Carbohydrate Polymers:

Carbohydrate polymers may be selected from pectin, starch, modified starch, cellulose, modified cellulose, carrageenan, gum Arabic, acacia gum, xanthan gum, locust bean gum, guar gum, polysaccharides e.g. Hyaluronic acid and dextrin. As employed in the context of the present invention, the term "modified starch" denotes a starch (native starch), which has undergone some kind of at least partial chemical modification, enzymatic modification, and/or physical or physicochemical modification, and which—in general—exhibits altered properties relative to the "parent" starch.

Relevant chemical modifications include, but are not limited to: esterification of hydroxy groups (achieved, e.g. via acetylation); etherification of hydroxy groups; oxidation (achieved, e.g. via reaction with chlorine or hypochlorite); and cross-linking (achieved, e.g. by reaction with formaldehyde or epichlorohydrin).

Relevant enzymatic modifications include, for example, treatment with a starch-degrading or starch-modifying enzyme, e.g. an amylase, such as an alpha-amylase or glucoamytase.

Relevant physical or physicochemical modifications include, in particular, so-called gelatinisation. The term "gelatinised", in the context of starch, is used herein in accordance with usage in the art (see, e.g. A. Xu and P. A. Seib, Cereal Chem. 70 (1993), pp. 463-470).

Synthetic Polymers:

Synthetic polymers may be selected from but are not limited to the group consisting of polyvinyl pyrrolidone (PVP), polyvinyl alcohol (PVA), polyvinyl acetate, polyacrylate, polymethacrylate, poly-acrylamide, polysulfonate, polycarboxylate, and copolymers thereof, in particular water soluble polymers or copolymers. The coating may also contain one or more conventional coating materials, in particular materials, which are soluble or dispersible in water. Conventional coating materials are described e.g. in WO 89/08694, WO 89/08695, EP 270608 B1 and/or WO 00/01793. Other examples of conventional coating materials may be found in U.S. Pat. No. 4,106,991, EP 170360, EP 304332, EP 304331, EP 458849, EP 458845, WO 97/39116, WO 92/12645A, WO 87/07292, WO 91/06638, WO 92/13030, WO 93/07260, WO 93/07263, WO 96/38527, WO 96/16151, WO 97/23606, U.S. Pat. No. 5,324,649, U.S. Pat. No. 4,689,297, EP 206417, EP 193829, DE 4344215, DE 4322229 A, DD 263790, JP 61162185 A and/or JP 58179492.

Auxiliary Coating Materials

The coating solution may further comprise coating materials selected from solvents, enzyme stabilizers, salts, inorganics, plasticizers, chlorine scavengers, fibers, water insoluble minerals, pigments, lubricants (such as surfactants or antistatic agents), waxes, fragrances, hollow/light particles or combinations thereof.

Solvents:

Suitable solvents can be but are not limited to alcohols and water.

In one embodiment of the present invention the solvent is water, i.e. the liquid coating composition is an aqueous dispersion and/or solution.

Enzyme Stabilising Agents:

Enzyme stabilising or protective agents such as conventionally used in the field of granulation may be elements of the coating. Stabilising or protective agents may fall into several categories: alkaline or neutral materials, reducing agents, antioxidants and/or salts of first transition series metal ions. Each of these may be used in conjunction with other protective agents of the same or different categories. Examples of alkaline protective agents are alkali metal silicates, carbonates or bicarbonates, which provide a chemical scavenging effect by actively neutralising e.g. oxidants. Examples of reducing protective agents are salts of sulfite, thiosulfite, thiosulfate or MnSO$_4$ while examples of antioxidants are methionine, butylated hydroxytoluene (BHT) or butylated hydroxyanisol (BHA). In particular stabilising agents may be salts of thiosulfates, e.g. sodium thiosulfate or methionine. Also enzyme stabilizers may be borates, borax, formates, di- and tricarboxylic acids and reversible enzyme inhibitors such as organic compounds with sulfhydryl groups or alkylated or arylated boric acids. Examples of boron based stabilizer may be found in WO 96/21716, whereas a preferred boron based stabilizer is 4-Formyl-Phenyl-Boronic Acid or derivatives thereof described in WO 96/41859 both disclosures incorporated herein by reference. Still other examples of useful enzyme stabilizers are gelatine, casein, Poly vinyl pyrrolidone (PVP) and powder of skimmed milk. The amounts of protective agent in the coating may be 5-40% w/w of the coating, particularly 5-30%, e.g. 10-20%.

Salts:

The salt may be an inorganic salt, e.g. salts of sulfate, sulfite, phosphate, phosphonate, nitrate, chloride or carbonate or salts of simple organic acids (less than 10 carbon atoms e.g. 6 or less carbon atoms) such as citrate, malonate or acetate. Examples of cations in these salt are alkali or earth alkali metal ions, although the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used. Specific examples include NaH$_2$PO$_4$, Na$_2$HPO$_4$, Na$_3$PO$_4$, (NH$_4$)H$_2$PO$_4$, K$_2$HPO$_4$, KH$_2$PO$_4$, Na$_2$SO$_4$, K$_2$SO$_4$, KHSO$_4$, ZnSO$_4$, MgSO$_4$, CuSO$_4$, Mg(NO$_3$)$_2$, (NH$_4$)$_2$SO$_4$, sodium borate, magnesium acetate and sodium citrate.

The salt may also be a hydrated salt, i.e. a crystalline salt hydrate with bound water(s) of crystallization, such as described in WO 99/32595. Examples of hydrated salts include magnesium sulfate heptahydrate (MgSO$_4$(7H$_2$O)), zinc sulfate heptahydrate ($ZnSO_4(7H_2O)$), copper sulfate pentahydrate ($CuSO_4(5H_2O)$), sodium phosphate dibasic heptahydrate ($Na_2HPO_4(7H_2O)$), magnesium nitrate hexahydrate ($Mg(NO_3)_2(6H_2O)$), sodium borate decahydrate, sodium citrate dihydrate and magnesium acetate tetrahydrate.

Plasticisers:

By adding various plasticizers to the polymer solution, e.g. PVA and/or Glycerol, different levels of tackiness of the filaments can be achieved, and the mechanical properties of the filaments can be changed, e.g. lower glass transition temperature ($T_g$).

Plasticizers useful in coating layers in the context of the present invention include, for example: polyols such as sugars, sugar alcohols, glycerine, glycerol trimethylol propane, polyvinyl alcohol (PVA), neopentyl glycol, triethanolamine, mono-, di- and triethylene glycol or polyethylene glycols (PEGs) having a molecular weight less than 1000; urea, phthalate esters such as dibutyl or dimethyl phthalate; thiocyanates, non-ionic surfactants such as ethoxylated alcohols and ethoxylated phosphates and water.

Inorganics:

Inorganics such as water soluble and/or insoluble inorganic salts such as finely ground alkali sulphate, alkali carbonate and/or alkali chloride, clays such as kaolin (e.g. SPESWHITE™, English China Clay). mineral fillers, bentonites, taics, zeobtes, calcium carbonate, silica e.g. fumed silica and/or silicates.

Fibers:

Fibre materials such as pure or impure cellulose In fibrous form. This can be sawdust, pure fibrous cellulose, cotton, or other forms of pure or impure fibrous cellulose. Also, filter aids based on fibrous cellulose can be used. Several brands of cellulose In fibrous form are on the market, e.g. CEPO™ and ARBOCEL™. Pertinent examples of fibrous cellulose filter aids are ARBOCEL BFC200™ and ARBOCEL BC200™. Also synthetic fibers may be used as described in EP 304331 B1 and typical fibers may be made of polyethylene, polypropylene, polyester, especially nylon, polyvinylformate, poly (meth)acrylic compounds.

Pigments:

Suitable pigments include, but are not limited to, finely divided whiteners, such as titanium dioxide or kaolin, coloured pigments, water soluble colorants, as well as combinations of one or more pigments and water soluble colorants.

Lubricants:

As used in the present context, the term "lubricant" refers to any agent, which reduces surface friction, lubricates the surface of the granule, decreases tendency to build-up of static electricity, and/or reduces friability of the granules. Lubricants can also play a related role in improving the coating process, by reducing the tackiness of polymers in the coating. Thus, lubricants can serve as anti-agglomeration agents and wetting agents.

Examples of suitable lubricants are lower polyethylene glycols (PEGs), ethoxylated fatty alcohols and mineral oils. The lubricant is particularly a mineral oil or a nonionic surfactant, and more particularly the lubricant is not miscible with the other coating materials.

Waxes:

Waxes may be the ones described in the section "Coating substances". Suitable waxes may further be water insoluble waxes, which are dispersible in an aqueous solution such as triglycerides and oils.

Examples of such waxes are hydrogenated ox tallow, hydrogenated palm oil, hydrogenated cotton seeds and/or hydrogenated soy bean oil, wherein the term "hydrogenated" as used herein is to be construed as saturation of unsaturated carbohydrate chains, e.g. in triglycerides, wherein carbon=carbon double bonds are converted to carbon-carbon single bonds. Hydrogenated palm oil is commercially available e.g. from Hobum Oele und Fette GmbH—Germany or Deutche Cargill GmbH—Germany.

Surfactants:

Surfactants may be non-ionic including semi-polar and/or anionic and/or cationic and/or zwitterionic.

Suitable anionic surfactants are linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

Suitable non-ionic surfactants are alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

Hollow/Light Particles:

Hollow/light particles are small particles with low true density. Typically, they are hollow spherical particles with air or gas inside. Such materials are usually prepared by expanding a solid material. These light spheres may be inorganic of nature such as SCOTCHLITE™ Glass Bubbles from 3M™ (hollow glass spheres), Q-CEL® (hoNow microspheres of borosilicate glass) and/or Extendospheres® (ceramic hollow spheres) available from The PQ Corporation. The light spheres may also be of organic nature such as the PM-series (plastic hollow spheres) available from The PQ Corporation. Expance® (hollow plastic spheres) from AKZO Nobel, Luxsil® and Sphericel® from Potters Industries andlor Styrocell® fran, SHELL, which is spheres of polystyrene. The polystyrene of Styrocel® contains pentane which upon heating boils and expands or pops the material (the reaction is comparable to the expansion of corn seeds into popcorn) leaving a light polystyrene material of a low true density. Also potyseocharides are preferred, such as starch or derivatives thereof. Biodac® is an example of non-hollow lightweight material made from cellulose (waste from papemaking), available from GranTek Inc.

Some of the auxiliary coating materials and coating substances may be on a particulate form and as such referred to as particulate matter. in the context of the present Invention the term particulate matter is to be understood as solid particles, particularly having a predominantly spherical shape, having an average diameter in its longest dimension, which is less than the thickness of the coating, in particular particles having an average diameter in its longest dimension below 50 microns. In a particular embodiment the particulate-matter can pass a 50 micron×50 micron sieve. In a particular embodiment of the present invention the fibers suitable in the present invention have a length in its longest dimension below 1000 microns and a width in it shortest dimension below 50 microns.

Particulate matter and other coating substances can be selected from but are not limited to fragrances, hollow spheres, light spheres, fibers, salts, water insoluble minerals, inorganics, pigments, enzyme stabilizers, protective agents, waxes, chlorine scavengers, lubricants (such as surfactants or antistatic agents) as mentioned vide supra, the particulate matter and other coating substances can further be selected from any conventional detergent ingredient as mentioned in the section "Detergents".

It was found that the construction of the coating did result in a coating containing a significant amount of gas.

The gas component is to be understood as any gas or mixture of gases, such as atmospheric air, carbon dioxide, nitrogen, noble gases. In a particular embodiment the gas phase component is atmospheric air. In a particular embodiment of the present invention the gas component constitutes at least 25% by volume of the coating, in a further particular embodiment of the present invention the gas component constitutes at least 50% by volume of the coating.

The coating may perform any of a number of functions in the particle or granule, depending on the intended use. Thus, for example, a coating may achieve one or more of the following effects:
(i) further reduction of the dust-formation tendency of a core particle;
(ii) further protection of active(s) in the core particle against oxidation by bleaching substances/systems (e.g. perborates, percarbonates, organic peracids and the like);
(iii) dissolution at a desired rate upon introduction of the particle into a liquid medium (such as an aqueous medium);
(iv) provide a more elastic coating which improves the impact resistance of the particle of the invention.
(v) provide more functionalities to the particle e.g. fragrance, colour, reduce density, increase anti-agglomeration.

Process for Preparing Granules

Preparing Core Particles

Methods for preparing core particles include those disclosed in the above mentioned references, i.e. a)spray dried products, b)layered products, c)absorbed products, d)extrusion or pelletized products, e)prilled products and f)mixer granulation products.

Methods for preparing a visco-elastic liquid core particle include those described in PA 2000 01459.

Methods for preparing a visco-elastic liquid core particles should always contain the step of dispersing the active and optionally other materials, preferably in a dry solid particulate form, in a visco-elastic liquid matrix to a preferably homogenous dispersion. This step could suitably be conducted at elevated temperatures to gain a lower viscosity than that of the finished particles. However, due care should be taken in not damaging the active by the heat. In this context an important feature is that the visco-elastic liquid matrix has a low amount of water, because the absence of water may make it possible to apply higher temperatures than if water was present without significantly damaging the active.

After preparing this mixture a number of different step can be applied to prepare liquid particles from the dispersion.

In one embodiment the dispersion is cooled to freeze and the dispersion is crushed and/or grinded to obtain small particles of the frozen liquid.

In another embodiment the dispersion is processed while the visco-elastic liquid matrix is in its liquid state by rolling the dispersion into a thin sheet of visco-elastic liquid material and cutting out pieces. This method resembles the way Italian pasta is made by preparing sheets of material and slicing pieces of a desired shape from the sheet.

In a third embodiment the dispersion is extruded through a small hole and cut into small pieces The particles obtained in the above mentioned is preferably rounded to achieve spherical or near spherical shape of the particles. This can be done conventionally, such as in a Marumarizer. It is however preferred to use liquid nature of the particles to shape to particles. By fluidising the particles in a fluid bed dryer and subjecting the particles to heat the surface tension of the visco-elastic liquid matrix will cause the particles to adapt a spherical shape. This procedure also facilitates any subsequent coating step because application of the coating may be conducted after rounding of the particles, but while the particles are still fluidised. In a fluid bed coating process the fluidised core particles are sprayed with a solution containing the coating material(s), and the coating is deposited on the surface of the core particles by evaporating the solution solvent.

Preparing the Coating

Preparation of Filaments by Atomization of a Liquid Coating Composition:

One way of providing a liquid coating composition comprising a substance which upon atomization of the liquid adopts a filamentous form as filaments is to adjust the rheolocical properties by adjusting the molecular weight of the polymer and/or temperature and/or solid content of the polymer solution optionally in combination, it is thereby possible to obtain a liquid coating composition having a sufficiently high elongational viscosity so that when atomizing the liquid coating composition, filaments are formed in stead of single droplets. Such liquids can be said to have exceeded the atomization limit. The atomization limit may further be dependent on process conditions being method or process parameters. Process parameters effecting the atomization limit can be but are not limited to temperature, pressure, air flow, liquid pressure e.g. during hydraulic atomization or rotational speed e.g. during centrifugal atomization.

Elongational viscosity of liquid solutions which are non-Newtonian, describes the resistance to extension, while the common viscosity term describes the resistance to shearing. Elongational viscosity is described in Bird R. B.; Armstrong R. C., Hassager O. "Dynamics of polymeric liquids", Volume 1: Fluid mechanics, John Wiley and Sons, Chapter 6, especially page 185-189, 1977, it is hereby incorporated herein by reference.

By atomization limit is meant the point at which liquids upon atomization forms filaments instead of droplets.

In a particular embodiment of the present invention one liquid coating composition is atomized onto particles as filaments. In a more particular embodiment of the present invention two liquid coating compositions are atomized onto particles as filaments either applying one filamentous coating after the other or applying the filamentous coatings simultaneously.

In a particular embodiment of the present invention the coating comprises above 60% by weight of filaments. In a more particular embodiment of the present invention the coating comprises above 80% by weight of filaments.

Adding Particulate Matter and other Coating Substances:

We have furthermore surprisingly found that the formed filaments may be used as an efficient way of layering particulate matter and other coating substances, e.g. perfume, onto the surface of the particle to be coated, which allows for adding more functionalities/properties to the coating being e.g. color, odor, increase anti-agglomeration, reduce hygroscopicity, reduce density of the coat by increased porosity and improvement in impact resistance of the granule.

Furthermore it is known that when some desirable detergent materials are mixed in liquid formulations undesirable reactions may take place e.g. acid/carbonate reactions, but when layered as dry particles as in the present invention it is possible to include both materials in the formulation.

One or more of these particulate matter or coating substances may be added before, simultaneously with or after applying the liquid coating composition which forms filaments.

Suitable particulate matter or other coating substances of the present invention are mentioned vide supra in the sections "Coating substances" and "Auxiliary coating materials".

One way of adding particulate matter or other coating substances is in a fluid bed.

Coating Methods:

In a particular embodiment of the present invention the coated granule may be prepared by a method comprising the following steps:
 (i) providing a liquid coating composition, which forms filaments when atomized,
 (ii) applying the liquid coating composition by the use of a atomization device to an active containing particle in a coating chamber, the method may further comprise the following step:
 (iii) applying particulate matter prior, simultaneous or subsequent to applying the liquid coating feed to the active containing particle in the coating chamber.

In a particular embodiment of the present invention the coated granule may be prepared by a process for preparing coated granules comprising contacting a particle comprising an active compound with a coating material, wherein the coating material comprises filaments prepared from atomizing a liquid coating composition having the property that said liquid coating composition forms filaments upon atomization during coating of the cores.

After leaving the nozzle the liquid coating composition and the particulate matter enters a coating chamber. The coating chamber may be any of a number of coating chambers known per se. Thus said chamber could be in the form of a coating device, wherein the liquid coating composition, the particulate matter as well as the active containing particles to be coated enters the coating chamber in the upper part thereof. The active containing particles become coated and dried on their way down the coating chamber and leave said chamber in the lower part thereof. A representative example of said embodiment is shown in U.S. Pat. No. 5,993,549.

Alternatively, the coating chamber may be a fluid-bed apparatus, wherein the coating composition incorporating the particulate matter as disclosed above enters the chamber at the bottom thereof. The fluid-bed chamber comprises housing for containing the core particles to be coated and a base plate positioned and arranged at the bottom of said housing. A particularly preferred embodiment of said apparatus is disclosed in U.S. Pat. No. 5,718,764, the contents of which are incorporated herein by reference.

In a particular embodiment of the process according to the invention said process comprises a combination of a fluid-bed coating and drying of the particles whereby a first layer of coating material is applied to the core particles at the bottom of the fluid-bed. The coated particles then rise through one or several draft tubes mounted vertically in the fluid-bed wherein the air-flow is increased compared to outside the tubes. As the coated particles rise through the tubes they will dry and after leaving the tubes the particles will slowly drift to the bottom of the fluid-bed where they will re-enter the draft tubes for further coating. Since the coated particles are dried in said tubes, less agglomeration and consequently more evenly coated particles are obtained.

U.S. Pat. No. 5,236,503 describes a fluid-bed Wurster coater, in which one or more draft tubes, each containing a nozzle, are mounted vertically in the fluid-bed.

In a further embodiment of the process according to the invention the coating chamber is a fluid-bed having a container and a circle of guide vanes, e.g. as disclosed in EP 0541759B1, EP 0436787B1, EP 0370167B1, and EP 0212397A2, all to Hüttlin.

The coated particle will typically be between 50 to 2000 microns. When the particle is used in detergents it will usually be between 400 to 700 microns and when used within the baking industry it will usually be between 50 to 200 microns.

The atomization device may suitably be selected from high speed rotating disk atomizers, pressure nozzle atomizers e.g. hydraulic, pneumatic nozzle atomizers or sonic nozzle atomizers such as described in the Course Material from the Microencapsulation Seminar, held by Center for professional advancement on May 9 to May 11, 1990 in Amsterdam.

In a particular embodiment of the present invention the nozzle used is a multi fluid nozzle. In a more particular embodiment the nozzle used according to the invention is a two fluid nozzle or a three fluid nozzle.

In a particular embodiment of the present invention the nozzle used is a two fluid nozzle, wherein one medium is the particulate matter and the other medium is the liquid coating composition.

If the coating is applied to a core particles in a fluid bed the temperature of the coating will typically be between 0 to 100° C., particularly between 10 to 90° C., more particularly between 10 to 80° C. or most particularly between 10 to 70° C. The Inlet air-temperature in the fluid bed will typically be between 40 to 200° C., particularly between 40 to 100° C.C, more particularly between 40 to 80° C.

Using Preformed Filaments

An elastic coating with improved impact resistance can also be prepared from preformed filaments. The preformed filaments may during the coating process build up a "ball of yarn" like appearance and the coating may become elastic and lightweight. The filaments adhere to the surface of the particles, e.g. by applying a molten wax e.g. PEG, nonionic surfactants, or other adhesive material. One way of applying the filaments to the surface of active containing particles is to mix the filaments, adhesive materials and auxiliary coating materials together with the active containing particles in a mixer apparatus. The filaments can also be applied to the surface via a suspension of the filaments in a liquid, which is sprayed onto the particles in a fluid bed.

In a particular embodiment of the present invention the coating comprises 5-95% by weight of material in filamentous form. In a more particular embodiment of the present invention the coating comprises 25-75% by weight of material in filamentous form. In an even more particular embodiment of the invention the coating comprises above 40% by weight of material in filamentous form. In a most particular embodiment of the present invention the coating comprises above 60% by weight of material in filamentous form.

In a particular embodiment of the invention the filament length is between 10 to 4000 microns in a more particular embodiment of the invention the filament length is 20 to 1000 microns, In an even more particular embodiment of the invention the filament length is 100 to 1000 microns.

In a particular embodiment of the invention the filament diameter is between 0.5 to 50 microns, in a more particular embodiment of the invention the filament diameter is between 5 to 30 microns.

Filaments suitable for this coating are natural or man-made filaments. The natural filaments are particularly plant filaments e.g. cellulosic filaments, pure filamentous cellulose, cotton, or other forms of pure or impure filamentous cellulose. Also, finer aids based on filamentous cellulose can be used. Several brands of cellulose In filamentous form are on the market, e.g. CEPO™ and ARBOCELL™ Pertinent examples of filamentous cellulose filter aids are Arbocel BFC200™ and Arbocel BC200™. Filaments from soft-wood or hard-wood. Man-made filaments such as regenerated natural filaments, synthetic filaments as described in EP 304331 B1 or mineral filaments. In a particular embodiment of the invention the filaments are hollow. In a more particular embodiment the filaments are hollow cellulose fibers.

The polymers used for these filaments are selected between but are not limited to rayon, acetate, nylon, polyamide, acrylate, olefins, polyethylene, polypropylene, vinylon, polyester, polyvinylformate, poly(meth)acrylic compounds.

As adhesive substance following polymers are suitable: waxes, polypeptides, carbohydrate polymers and synthetic polymers as mentioned in the section "Coating substances". The coating may further comprise additional coating materials as mentioned in the section "Auxiliary coating materials". Conventional coating materials are further described e.g. in WO 89/08694, WO 89/08695, EP 270608 B1 and/or WO 00/01793. Other examples of conventional coating materials may be found in U.S. Pat. No. 4,106,991, EP 170360, EP 304332, EP 304331, EP 458849, EP 458845, WO 97/39116, WO 92/12645A, WO 87/07292, WO 91/06638, WO 92/13030, WO 93/07260, WO 93/07263, WO 96/38527, WO 96/16151, WO 97/23606, U.S. Pat. No. 5,324,649, U.S. Pat. No. 4,689,297, EP 206417, EP 193829, DE 4344215, DE 4322229A, DD 263790, JP 61162185A and/or JP 58179492.

In a particular embodiment of the invention the adhesive substance is a wax.

The filaments may be applied to the surface of an active containing particle or granule in a coating chamber, the coating chamber may be any of a number of coating chambers known per se. The coating may be applied to the core particles using any conventional coating method such as in a mixer or in a fluid bed. In a particular embodiment of the fluid bed coating process, the fluidised core particles are sprayed with a solution containing the coating material(s) and the coating is deposited on the surface of the core particles by evaporating the solution solvent, see e.g. U.S. Pat. No. 6,136,772. Further suitable coating methods and apparatus are described vide infra in the section "Coating methods".

If the coating comprises a wax and it is applied in a mixer the mixer temperature should be higher than the melting temperature of the wax. This will typically lie between 30 and 100° C.

In a particular embodiment of the invention the filaments are applied to an active containing particle in a mixer apparatus e.g. a Lödige mixer, a roller device or a spraying device e.g. a fluid bed.

In a particular embodiment of the invention one or more type of filaments is applied to an active containing particle.

It is further possible to incorporate particulate matter e.g. light spheres in the filamentous coating by adding them to the coating chamber together with the filaments. Suitable particulate matter is mentioned vide supra.

Compositions Comprising the Coated Particle and Their Application

The invention also relates to compositions comprising the coated particles of the invention. The composition may be any composition, but particularly the compositions are well suited for use in the feed, textile, food, baking and/or detergent industry. Accordingly the compositions may be animal feed compositions, food compositions, e.g. in baking; baker's flour, dough, or detergent composition, or to use in the treatment of textiles or an additive to be incorporated in such compositions. Also the invention encompasses the use of the compositiion, e.g. for improving foodstuffs such as bread or for cleaning an object such as a cellulose containing fabric.

Feed

In a particular embodiment of the invention we have found that the granules of our invention are useful in animal feed compositions.

Baking

In a special embodiment of the invention we have found that our development of coated particles comprising an active is useful in baking industry.

Within the flour mill and the baking industry the use of actives, such as enzymes, is well established. Accordingly the invention provides baking compositions comprising the coated particles of the invention, in particular dough improver compositions or flour compositions comprising the dough improver.

When using enzymes in the baking industry certain enzyme activities are preferred. Flour has varying content of amylases leading to differences in the baking quality. Addition of amylases can be necessary in order to standardize the flour. Amylases and pentosanases generally provide sugar for the yeast fermentation, improve the bread volume, retard retrogradation, and decrease the staling rate and stickiness that results from pentosan gums. Examples of carbohydrases are given below.

Certain maltogenic amylases can be used for prolonging the shelf life of bread for two or more days without causing gumminess in the product. Selectively modifies the gelatinized starch by cleaving from the non-reducing end of the starch molecules, low molecular wight sugars and dextrins. The starch is modified in such a way that retrogradation is less likely to occur. The produced low-molecular-weight sugars improve the baked goods water retention capacity without creating the intermediate-length dextrins that result in gumminess in the finished product. The enzyme is inactivated during bread baking, so it can be considered a processing aid, which does not have to be declared on the label.

The bread volume can be improved by fungal alpha-amylases, which further provide good and uniform structure of the bread crumb.

Said alpha-amylases are endoenzymes that produce maltose, dextiins and glucose. Cereal and some bacterial alpha-amylases are inactivated at temperatures above the gelatinization temperature of starch, therefore when added to wheat dough it results in a low bread volume and a sticky bread interior. Fungamyl has the advantage of being thermolabile and is inactivated Just below the gelatinization temperature.

Enzyme preparations containing a number of pentosanase and hemi-cellulase activities can improve the handling and stability of the dough, and improves the freshness, the crumb structure and the volume of the bread.

By hydrolysing the pentosans fraction in flour, it will lose a great deal of its water-binding capacity, and the water will then be available for starch and gluten. The gluten becomes more pliable and extensible, and the starch gelatinizes more easily. Pentosanases can be used in combination with or as an alternative to emulsifiers.

Detergents

The coated particles of the invention may also be added to and thus become a component of a detergent composition.

The detergent composition of the invention may for example be formulated as laundry detergent composition for hand or machine washings including a cleaning additive composition suitable for pre-treatment of stained fabrics or a fabric softener composition, or a detergent composition for use in general household hard surface cleaning operations, or a composition for hand or machine dishwashing operations.

In a specific aspect, the invention provides a detergent additive comprising the coated particles of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include ALCALASE™, SAVINASE™, PRIMASE™, DURALASE™, ESPERASE™, and KANNASE™ (Novozymes A/S), MAXATASE™, MAXACAL™, MAXAPEM™, PROPERASE™, PURAFECT™, PURAFECT OXP™, FN2™, and FN3™(Genencor International Inc.).

Lipases: Suitable lipases include those of bacterial or fungal origin. Chemically modified or protein engineered mutants are included. Examples of useful lipases include lipases from *Humicola* (synonym Thermomyces), e.g. from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASE™ and LIPOLASE ULTRA™ (Novozymes A/S).

Amylases: Suitable amylases (alpha and/or beta) include those of bacterial or fungal origin. Chemically modified or protein engineered mutants are included. Amylases Include, for example, alpha-amylases obtained from *Bacillus*, e.g. a special strain of *B. lichenifomils*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are DURAMYL™, TERMAMYL™, FUNGAMYL™ and BAN™ (Novozymes A/S), RAPIDASE™ and PURASTAR™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include CELLUZYME™, and CAREZYME™ (Novozymes A/S), CLAZINASE™, and PURADAX HA™ (Genencor International Inc), and KAC-500™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from Coprinus, e.g. from *C. cinereus*, and variants thereof as those described in WO 93/24618, WO 95/10602, and WO 98/15257.

Commercially available peroxidases include GUARDZME™ (Novozymes A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, may be formulated so as to contain one or more of the particles of the invention comprising different enzymes.

The detergent composition of the invention may be in any convenient dry form, e.g., a bar, a tablet, a powder, a granule or a paste. It may also be a liquid detergent, in particular non-aqueous liquid detergent.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system, which may comprise a $H_2O_2$ source such as perborate or percarbonate, which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, may be added in an amount corresponding to 0.01-100 mg of enzyme protein per litre of wash liquor, preferably 0.05-5 mg of enzyme protein per litre of wash liquor, in particular 0.1-1 mg of enzyme protein per litre of wash liquor.

The enzyme of the invention may additionally be incorporated in the detergent formulations disclosed in WO 97/07202, which is hereby incorporated as reference.

EXAMPLES

Example 1

A liquid coating composition able of forming filaments upon atomization according to the invention was prepared.

The liquid coating composition consisted of:

4 kg polyvinyl alcohol (PVA) (Moviol 4-88 obtainable from Hoechst, Germany) as polymer 0.4 kg glycerol (99.5%) as plasticizer 12 kg $H_2O$ (demineralised) as solvent The polymer was slowly dissolved in the water/glycerol mixture by heating for one hour at 85° C.

A GEA PrecisionCoater® was charged with 5 kg of active containing particles; Savinase 12 TX® enzyme product. The liquid coating composition described above was sprayed onto this batch of enzyme containing particles using a nozzle pressure of 3.8 bars. The inlet- and out let temperatures were 90° C. and 58-64° C. respectively. This corresponds to a liquid dosing rate of 59 g/min.

Continuously, Expancel®, light particles, was added co-axially around the nozzle suspended in the main air stream. The Expancel® particles serve two purposes. The first being control of the porosity of the layers of filaments and the second is reducing the stickiness of the filaments that otherwise would create excessive agglomeration of the final product.

The coated particles was characterised by their bulk- and apparent particle density. See Table 1. These values are listed as a function of amount of filament in % of uncoated material, which means that 10% is corresponding to 100 g of uncoated particle is coated with 10 g of filamentous material.

TABLE 1

Densities vs. amount of filamentous material in weight % of uncoated material.

| Product | Bulk density (g/ml) | Tapped density (g/ml) | Particle density (g/ml) |
| --- | --- | --- | --- |
| Uncoated material, 0% | 1.26 | 1.38 | 2.059 |
| 6% | 0.79 | 0.87 | 1.806 |
| 12% | 0.76 | 0.81 | 1.652 |
| 18% | 0.63 | 0.67 | 1.368 |
| 24% | 0.39 | 0.42 | 1.042 |

This example clearly shows a decrease in density by increasing the amount of filamentous coating material in the granule.

Example 2

The granules produced in example 1 were subsequently subjected to a special impact test In this test the granules were Individually accelerated to a speed of 10 m/s and thereafter impacted directly at a quarts surface at an angle of 90°. All particles were subjected to 13 consecutive impacts and the total amount of active enzyme protein released was measured.

The results are shown in table 2. It was surprisingly found that an optimal coating layer thickness was found. Applying either too little or too much material reduced the impact resistance. A thickness of the coating layer corresponding to 10 to 15% by weight of uncoated material was found to be optimal for product and process conditions used in this example. When too little filamentous coating was applied the layer was too thin and flexible to absorb the impact energy, which then damaged the standard PEG coating below. If a too large amount was applied the coating layer strength became comparable with the under laying PEG coating and correspondingly higher forces were transmitted into the PEG coating by the plastic deformation of the filamentous coating.

TABLE 2

Active dust released after 13 impacts vs. amount of filamentous material in weight % of uncoated material.

| Product Wt % of granule which are coating | Active dust after 13 impacts @ 10 m/s |
| --- | --- |
| Uncoated material, 0% | 809 ng/g |
| 6% | 709 ng/g |
| 12% | 209 ng/g |
| 18% | 238 ng/g |
| 24% | 466 ng/g |

Example 3

Uncoated Savinase granulate was produced as described in U.S. Pat. No. 4,106,991 example 1 with the following exceptions:

Sodium sulfate was used instead of sodium chloride as filler material

The enzyme concentrate (added as a liquid) contained also a carbohydrate binder (Avedex W80 dextrin) and sodium thiosulfate as an antioxidant.

Three granulates were produced by coating the above uncoated particles in a Lödige mixer with:

A: 10.0% PEG 4000, 4.4% Titan dioxide and 4.4% kaolin (as reference)

B: 10.0% PEG 4000 and 10% cellulose filaments (Arbocel BC200).

C: 12.0% PEG 4000 and 10.5% cellulose filaments (Arbocel BC200).

The particles were heated to 55° C. in a jacketed Lödige mixer M 20. The hot particles were sprayed with the polyethylene glycol 4000, which had been heated to 60° C., during continuous mixing. After distribution of PEG 4000 the granulates were layered with additional coating material 4.4% titanium dioxide and 4.4% Kaolin (reference) or 10.0/12% cellulose filaments during continuous mixing, $TiO_2$ being used as a whitening agent.

All percentages are based on the weight of the dry uncoated granulate.

The granulates were sieved between 300 and 1200 microns.

TABLE 3

Measured bulk density of the three granules.

| Granulate | Bulk density g/ml |
|---|---|
| A | 1.14 |
| B | 0.90 |
| C | 0.81 |

This example clearly demonstrates that the bulk density is lowered by making a fibrous coating. The granulates were sieved between 600 and 850 microns and the bulk compressibility was measured using a Stable Micro Systems Texture Analyzer. The granulates were compressed up to a force of 10 kg with a 20 mm piston, and the volume decrease was measured:

| Granular | Volume decrease |
|---|---|
| A | 5.5% |
| B | 10.0% |
| C | 13.6% |

The compressibility of the fibre coated granulates are significantly higher than for the reference. The higher compressibility is the larger deformations the granules may withstand before reaching the critical yield stress, where damage starts to occur. Consequently, the B and C product will be more impact resistant than the reference product A.

The invention claimed is:

1. A process for preparing a coated granule comprising:
    (a) atomizing a liquid coating composition which forms filaments upon atomization to produce a coating material which comprises filaments; and
    (b) contacting a particle comprising an enzyme with the coating material.

2. The process of claim 1, wherein step (a) comprises simultaneous atomization of at least two different liquid coating compositions which form filaments upon atomization to produce the filamentous coating.

3. The process of claim 2, wherein the simultaneous atomization is achieved by means of a multi-fluid nozzle.

4. The process of claim 3, wherein the multi-fluid nozzle is a two fluid nozzle or a three fluid nozzle.

5. The process of claim 1, wherein the contacting takes place in a coating chamber.

6. The process of claim 5, wherein said coating chamber is a fluid bed.

7. A process for preparing a coated granule, comprising:
    (a) atomizing a liquid coating composition which forms filaments upon atomization, during coating of a core to form a coating material which comprises filaments; and
    (b) contacting a particle comprising an enzyme with the coating material.

8. A process for preparing a coated granule comprising a core and a fliamentous coating, wherein the core comprises an enzyme and the filamentous coating comprises a porous network of filaments, the process comprising:
    (a) atomizing a liquid coating composition which forms filaments upon atomization to produce a coating material which comprises filaments; and
    (b) contacting a particle comprising an enzyme with the coating material.

9. A process in accordance with claim 8, wherein the core comprises an enzyme and the filamentous coating comprises a porous network of filaments in an amount above 60% by weight of the filamentous coating.

10. A process in accordance with claim 8, wherein the porous network of filaments comprises one or more polymers.

11. A process in accordance with claim 10, wherein the one or more polymers are selected from the group of waxes, polypeptides, carbohydrate polymers and synthetic polymers.

12. A process in accordance with claim 11, wherein the polypeptide is gelatin, collagen, casein, chitosan, polyaspartic acid or polyglutamic acid.

13. A process in accordance with claim 11, wherein the carbohydrate polymer is a polysaccharide.

14. A process in accordance with claim 13, wherein the polysaccharide is hyaluronic acid.

15. A process in accordance with claim 11, wherein the synthetic polymer is polyvinyl pyrrolidone (PVP), polyvinyl alcohol (PVA), polyvinyl acetate, polyacrylate, polymethacrylate, polyacrylamide, polysulfonate, polycarboxylate, or a copolymer thereof.

16. A process in accordance with claim 10, wherein the one or more polymers are in liquid form.

17. A process in accordance with claim 10, wherein the one or more polymers are dissolved, suspended, or emulsified in the liquid coating composition.

18. A process in accordance with claim 8, wherein the porous network of filaments comprises 25% to 75% by weight of polymers.

19. A process in accordance with claim 8, wherein the porous network of filaments comprises auxiliary coating materials.

20. A process in accordance with claim 19, wherein the auxiliary coating materials are selected from the group consisting of solvents, enzyme stabilizers, protective agents, salts, pigments, fibers, fragrances, inorganics, plasticizers, chlorine scavengers, water insoluble minerals, lubricants, surfactants, antistatic agents, hollow particles or light particles.

21. A process in accordance with claim 20, wherein the plasticizer is selected from the group of sugars, sugar alcohols, glycerine, glycerol trimethylol propane, polyvinyl alcohol (PVA), neopentyl glycol, triethanolamine, mono-, di- and triethylene glycol or polyethylene glycols (PEGs), urea, phthalate esters such as dibutyl or dimethyl phthalate; thiocyanates, non-ionic surfactants such as ethoxylated alcohols and ethoxylated phosphates and water.

22. A process in accordance with claim 20, wherein the salts, pigments, inorganics, water insoluble minerals, hollow particles or light particles are in a particulate form as particulate matter and are suspended in the porous network of fibers.

23. A process in accordance with claim 22, wherein the particulate matter is predominantly spherical shaped and has an average diameter in their longest dimension of less than the thickness of the coating.

24. A process in accordance with claim 8, wherein the filamentous coating is disposed upon the core in an amount of 10% to 15% by weight of the core.

25. A process in accordance with claim 8, wherein the coating comprises materials selected from the group consisting of solvents, enzyme stabilizers, salts, inorganics, clays, plasticizers, chlorine scavengers, fibers, water insoluble minerals, pigments, lubricants, surfactants, antistatic agents, waxes, fragrances, hollow/light particles and combinations thereof.

26. A process in accordance with claim 8, wherein the filamentous coating comprises at least 50% by volume of gas.

27. A process in accordance with claim 26, wherein the gas is atmospheric air, carbon dioxide, nitrogen or a noble gas.

28. A process in accordance with claim 8, wherein the filamentous coating comprises filaments prepared by atomizing at least two different liquid coating compositions which form filaments upon atomization.

29. A process in accordance with claim 8, wherein the filamentous coating comprises filaments in an amount above 80% by weight of coating.

30. A process in accordance with claim 8, wherein the enzyme is selected from the group consisting of oxidoreductase, transferase, hydrolase, lyase, isomerase, ligase, protease, amylase, lipase, cellulase, peroxidase, cutinase, carbohydrase, pectinase, mannanase, arabinase, galactanase, xylanase, oxidase, and combinations thereof.

* * * * *